United States Patent [19]

Buchel et al.

[11] 3,988,449
[45] Oct. 26, 1976

[54] TRISALKYL TIN 1,2,4-TRIAZOLE INSECTICIDAL AND ACARICIDAL AGENTS

[75] Inventors: Karl Heinz Büchel, Wuppertal-Elberfeld; Ingeborg Hammann, Cologne, both of Germany

[73] Assignee: Bayer Aktiengesellschaft, Leverkusen, Germany

[22] Filed: June 10, 1975

[21] Appl. No.: 585,644

Related U.S. Application Data

[62] Division of Ser. No. 280,622, Aug. 14, 1972, Pat. No. 3,907,818.

[30] Foreign Application Priority Data

Aug. 28, 1971  Germany............................ 2143252

[52] U.S. Cl. ................................................ 424/245
[51] Int. Cl.$^2$............................................ A01N 9/00
[58] Field of Search.................................... 424/245

[56] References Cited
UNITED STATES PATENTS
3,546,240  12/1970  Bublitz................................ 260/299

OTHER PUBLICATIONS

Luiten et al., "Recueil Des Travaux Chimiques Pays--Ras," 81 (1962), p. 202–205.

*Primary Examiner*—V. D. Turner
*Attorney, Agent, or Firm*—Burgess, Dinklage & Sprung

[57] ABSTRACT

Insecticidal and acaricidal compositions comprising, and methods of combating insects and acarids using, trisalkyl tin 1,2,4-triazoles of the formula

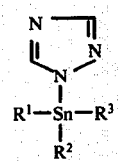

(I)

The compounds wherein $R^1$, $R^2$ and $R^3$ are branched alkyl or cycloalkyl are known.

9 Claims, No Drawings

TRISALKYL TIN 1,2,4-TRIAZOLE INSECTICIDAL AND ACARICIDAL AGENTS

This is a division of application Ser. No. 280,622 filed Aug. 14, 1972, now U.S. Pat. No. 3,907,818 issued Sept. 23, 1973.

The present invention relates to and has for its objects the combating of insects and acarids using trisalkyl tin 1,2,4-triazoles, i.e. tris-alkyl or cycloalkyl of up to 6 carbon atoms tin 1,2,4-triazoles, compositions containing such triazoles in the form of mixtures with solid and liquid dispersible carrier vehicles, preferably containing a surface-active agent, as well as the provision of new compounds, with other and further objects becoming apparent from a study of the within specification and accompanying examples.

It is known from H. Martin "Die wissenschaftlichen Grundlagen des Pflanzenschutzes", Verlag Chemie, Weinheim, Bergstrasse, (1967), p. 245; E. Y. Spencer "Guide to the Chemicals Used in Crop Protection", London, Ontario, Canada, pp. 471 and 472, 5th Edition, (1968); and German Patent Specification Abs. 950, 970 and 1,021,627, that certain organic tin compounds, for example triphenyl tin hydroxide (Compound A) and triphenyl tin acetate, (Compound B) exhibit some pesticidal effects.

Further, it is known from U.S. Pat. No. 3,546,240 that organotin azoles, particularly tricyclohexyl tin benzotriazole (Compound C), possess some pesticidal effectiveness.

The fungicidal and bactericidal effectiveness of further organotin azoles, in particular of triphenyl tin imidazole (Compound D), is the subject matter of U.S. application Ser. No. 19 84 27, filed Nov. 2, 1971, now abandoned. However, the insecticidal and acaricidal activity of the compounds, especially in the case of low applied amounts and concentrations, is not wholly satisfactory.

It has now surprisingly been found that the trisalkyl tin 1,2,4-triazoles of the formula

in which

R$^1$, R$^2$, R$^3$ each independently is alkyl or cycloalkyl of up to 6 carbon atoms exhibit very good insecticidal and acaricidal properties.

In formula (I), R$^1$, R$^2$ and R$^3$ are preferably the same. They stand for straight-chain or, preferably, branched alkyl with up to 6 carbon atoms, preferably with 3 to 6 carbon atoms, in particular isopropyl, sec.-butyl, or tert.-butyl; or for cycloalkyl with preferably 3 to 6 carbon atoms, in particular cyclohexyl and cyclopentyl.

Surprisingly, the trisalkyl tin azoles to be used according to the invention show a considerably higher insecticidal and acaricidal effectiveness than the tricyclohexyl tin benzotriazole known from the prior art or the triphenyl tin imidazole. The substances which can be used according to the invention therefore represent a valuable enrichment of the art.

As examples of the substances which can be used according to the invention, there are mentioned in particular:
tricyclohexyl-stannyl-1,2,4-triazole
tributyl-stannyl-1,2,4-triazole
tri-tertiarybutyl-stannyl-1,2,4-triazole
tris-isopropyl-stannyl-1,2,4-triazole
tri-sec.-butyl-stannyl-1,2,4-triazole
tri-pentyl-stannyl-1,2,4-triazole
tri-cyclopentyl-stannyl-1,2,4-triazole One of the substances which can be used according to the invention is already known, namely tributyl tin 1,2,4-triazole (Recueil des Travaux Chimiques des Pays-Bas 81 (1962) 202-205; Chimia 16 (1962) 10–15). Those which are not yet known can be prepared by heating bis-alkyl tin oxide with 1,2,4-triazole under reflux and azeotropically distilling off the water formed (cf. Recueil des Travaux Chimiques des Pays-Bas 81 (1962) 203 and Preparative Examples). Further, the substances of the formula (I) can also be obtained when the alkali metal salt of the azole is reacted with the tris-alkyl-stannylhalide concerned in liquid ammonia (cf. Recueil des Travaux Chimiques des Pays-Bas 81 (1962) 202-205) or in an organic solvent at temperatures between 0° and 100° C (cf. in U.S. Pat. No. 3,546,240).

Furthermore, the compounds to be used according to the invention can be prepared by reaction of a trisalkyl-stannylhalide with 1,2,4-triazole in a polar organic solvent in the temperature range between 50° and 150° C, preferably between 80° and 120° C, in the presence of an acid-binding agent which optionally, may be excess azoic; for reaction acceleration, potassium iodide may be added (cf. German Patent Application No. P 20 56 652.3).

As already mentioned, the active compounds according to the invention are distinguished by good insecticidal and acaricidal activity. Thus, they are to be used with particular advantage against plant-damaging mites and against sucking and biting insects.

To the sucking insects there belong, in the main, aphids (Aphidae) such as the green peach aphid (Myzus persicae), the bean aphid (Dotalis fabae), the bird cherry aphid (Rhopalosiphum padi), the pea aphid (Macrosiphum pisi) and the potato aphid (Macrosiphum solanifolii), the current gall aphid (Cryptomyzus korschelti), the rosy apple aphid (Sappaphis mali), the mealy plum aphid (Hyalopterus arundinis) and the cherry black-fly (Myzus cerasi); in addition, scales and mealybugs (Coccina), for example the oleander scale (Aspidiotus hederae) and the soft scale (Lecanium hesperidum) as well as the grape mealybug (Pseudococcus maritimus); thrips (Thysanoptera), such as Hercinothrips femoralis, and bugs, for example the beet bug (Piesma quadrata), the red cotton bug (Dysdercus intermedius), the bed bug (Cimex lectularius), the assassin bug (Rhodnius prolixus) and Chagas' bug (Triatoma infestans) and, further, cicadas, such as Euscelis bilobatus and Nephotettix bipunctatus.

In the case of the biting insects, above all there should be mentioned butterfly caterpillars (Lepidoptera) such as the diamond-back moth (Plutella maculipennis), the gipsy moth (Lymantria dispar), the browntail moth (Euproctis chrysorrhoea) and tent caterpillar (Malacosoma neustria); further, the cabbage moth (Mamestra brassicae) and the cutworm (Agrotis segetum), the large white butterfly (Pieris brassicae), the small winter moth (Cheimatobia brumata), the green oak tortrix moth (Tortrix viridana), the fall armyworm (Laphygma frugiperda) and cotton worm (Prodenia litura), the ermine moth (Hyponomeuta padella), the Mediterranean flour moth (*Ephestia buhniella*) and greater wax moth (*Galleria mellonella*).

Also to be classed with the biting insects are beetles (Coleoptera), for example the granary weevil (*Sitophilus granarius* = *Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*) the raspberry beetle (*Byturus tomentosus*), the bean weevil (Bruchidius = *Acanthoscelides obtectus*), the leather beetle (*Dermestes frischi*), the khapra beetle (*Trogoderma granarium*), the flour beetle (*Tribolium castaneum*), the northern corn billbug (Calandra or *Sitophilus zeamais*), the drugstore beetle (*Stegobium paniceum*), the yellow mealworm (*Tenebrio molitor*) and the saw-toothed grain beetle (*Oryzaephilus surinamensis*), but also species living in the soil, for example wireworms (*Agriotes* spec.) and larvae of the cockchafer (*Melolontha melolontha*); cockroaches, such as the German cockroach (*Blattella germanica*), American cockroach (*Periplaneta americana*), Madeira cockroach (Leucophaea or *Rhyparobia maderae*), oriental cockroach (*Blatta orientalis*), the giant cockroach (*Blaberus giganteus*) and the black giant cockroach (*Blaberus fuscus*) as well as Henschoutedenia flexivitta; further, Orthoptera, for example the house cricket (*Acheta domesticus*); termites such as the eastern subterranean termite (*Reticulitermes flavipes*) and Hymenoptera such as ants, for example the garden ant (*Lasius niger*).

The Diptera comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further, gnats, for example mosquitoes such as the yellow fever mosquito (*Aedes aegypti*), the northern house mosquito (*Culex pipiens*) and the malaria mosquito (*Anopheles stephensi*).

With the mites (Acari) there are classed, in particular, the spider mites (Tetranychidae) such as the two-spotted spider mite (*Tetranychus urticae*) and the European red mite (*Paratetranychus pilosus* (*Panonychus ulmi*), gall mites, for example the black currant gall mite (*Eriophyes ribis*) and tarsonemids, for example the broad mite (*Hemitarsonemus latus*) and the cyclamen mite (*Tarsonemus pallidus*); finally, ticks, such as the relapsing fever tick (*Ornithodorus moubata*).

When applied against hygiene pests and pests of stored products, particularly flies and mosquitoes, the process products are also distinguished by an outstanding residual activity on wood and clay, as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier solvents for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters and fatty acids, polyethylene oxide ethers of fatty alcohols, alkyl sulfates, alkyl sulfonates, aryl sulfonates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides and acaricides or rodenticides, fungicides, bactericides, nematocides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprises mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects and acarids, which comprises applying to at least one of correspondingly (a) such insects, (b) such acarids, and (c) the corresponding habitat thereof, i.e. the locus to be protected, a correspondingly combative or toxic amount, i.e. an insecticidally or acaricidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The synthesis, unexpected superiority and outstanding activity of the particular new compound of the present invention are illustrated, without limitation, by the following examples:

EXAMPLE 1

Tetranychus test/resistant

Solvent: 3 parts by weight dimethyl formamide
Emulsifier: 1 part by weight alkylaryl polyglycol ether To produce a suitable preparation of active compound, 1 part by weight of the active compound is mixed with the stated amount of solvent containing the stated amount of emulsifier and the concentrate so obtained is diluted with water to the desired concentration.

Bean plants (*Phaseolus vulgaris*), which have a height of approximately 10–30 cm., are sprayed with the preparation of the active compound until dripping wet. These bean plants are heavily infested with the two-spotted spider mite (*Tetranychus urticae*) in all stages of development.

After the specified periods of time, the effectiveness of the preparation of active compound is determined by counting the dead mites. The degree of destruction thus obtained is expressed as a percentage: 100% means that all the spider mites are killed whereas 0% means that none of the spider mites are killed.

The active compounds, the concentrations of the active compounds, the evaluation times and the results can be seen from the following Table 1:

Table 1

| Active compound | Concentration of active compound in % | Degree of destruction in % after 2 days |
|---|---|---|
| (A) (known) | 0.1 | 100 |
|  | 0.01 | 90 |
|  | 0.001 | 0 |
| (B) (known) | 0.1 | 100 |
|  | 0.01 | 95 |
|  | 0.001 | 20 |
| (D) (known) | 0.1 | 95 |
|  | 0.01 | 0 |
| (I) | 0.1 | 100 |
|  | 0.01 | 100 |
|  | 0.001 | 100 |
|  | 0.0001 | 95 |

(plant-damaging mites) Tetranychus test/resistant

EXAMPLE 2

Plutella test

Solvent: 3 parts by weight dimethyl formamide
Emulsifier: 1 part by weight alkylaryl polyglycol ether To produce a suitable preparation of active compound, 1 part by weight of the active compound is mixed with the stated amount by solvent containing the stated amount of emulsifier and the concentrate is diluted with water to the desired concentration.

Cabbage leaves (*Brassica oleracea*) are sprayed with the preparation of the active compound until dew moist and are then infested with caterpillars of the diamond-back moth (*Plutella maculipennis*).

After the specified periods of time, the degree of destruction is determined as a percentage: 100% means that all the caterpillars are killed whereas 0% means that none of the caterpillars are killed.

The active compounds, the concentrations of the active compounds, the evaluation times and the results can be seen from Table 2.

Table 2

| Active compounds | (plant damaging insects) Plutella test | |
|---|---|---|
| | Concentration of active compound in % | Degree of destruction in % after 3 days |
| 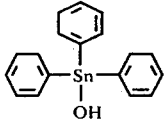 (A) (known) | 0.1 / 0.01 / 0.001 | 100 / 100 / 0 |
| 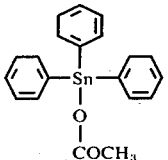 (B) (known) | 0.1 / 0.01 / 0.001 | 100 / 90 / 0 |
| 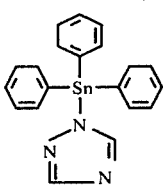 (D) (known) | 0.1 / 0.01 / 0.001 | 100 / 90 / 0 |
| 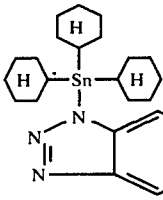 (C) | 0.1 / 0.01 / 0.001 | 100 / 100 / 0 |
| 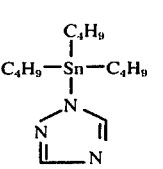 (2) | 0.1 / 0.01 / 0.001 | 100 / 100 / 80 |

The following further examples are set forth to illustrate, without limitation, the process for producing the active compounds according to the present invention.

EXAMPLE 3 a)

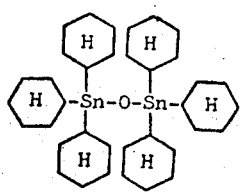

90 g (0.2 mole) of tricyclohexyltin bromide were dissolved in 500 ml of benzene, and 18 g of a 50%-strength sodium hydroxide solution were added dropwise. To complete the reaction, heating under reflux was effected for 3 hours, and thereafter the water was distilled off azeotropically. The sodium bromide formed was obtained practically quantitatively as a precipitate and was filtered off. The filtrate was evaporated to dryness in a vacuum. 70 g (46.5% of theory) of hexacyclohexyl tin oxide of the melting point 205° – 214° C were obtained.

b)

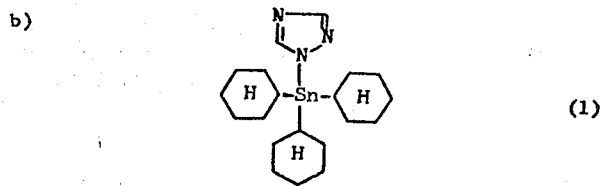 (1)

33 g (0.044 mole) of hexacyclohexyl tin oxide were dissolved in 700 ml of acetone, and 7 g (0.1 mole of 1,2,4-triazole were added dropwise at room temperature. Thereafter, the reaction solution was heated to the boil under reflux for 2 hours. After cooling, the precipitate was filtered off with suction, washed with anhydrous solvent and dried.

34 g (88.5% of theory) of tricyclohexyl tin 1,2,4-triazole of the melting point 209° – 211° C were obtained.

Analogously, the compounds of the following Table were prepared:

Table 3

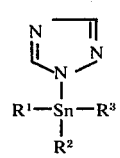

| Compound No. | $R^1$ | $R^2$ | $R^3$ | Melting point ° C |
|---|---|---|---|---|
| 2 | $C_4H_9$ | $C_4H_9$ | $C_4H_9$ | 61 – 66 |
| 3 | $CH(CH_3)_2$ | $CH(CH_3)_2$ | $CH(CH_3)_2$ | viscous oil |
| 4 | $C(CH_3)_3$ | $C(CH_3)_3$ | $C(CH_3)_3$ | viscous oil |
| 5 |  |  |  | 210 – 211 |

It will be appreciated that the instant specification and examples are set forth by way of illustration and not limitation, and that various modifications and changes may be made without departing from the spirit and scope of the present invention.

What is claimed is:
1. A method of combating insect or acarid pests which comprises applying to the pests or a habitat thereof an insecticidally or acaricidally effective amount of a trisalkyl tin 1,2,4-triazole of the formula

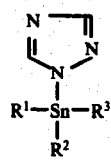 (I)

in which
R$^1$, R$^2$ and R$^3$ each independently is alkyl or cycloalkyl of 3 to 6 carbon atoms,
alone or in admixture with a diluent or carrier.

2. The method according to claim 1 in which R$^1$, R$^2$ and R$^3$ each is branched alkyl of 3 to 6 carbon atoms, cyclohexyl or cyclopentyl.

3. The method according to claim 1 wherein the trisalkyl tin 1,2,4-triazole is tricyclohexyl tin 1,2,4-triazole of the formula

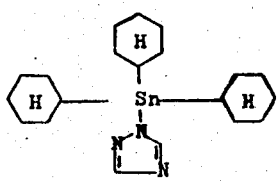 (1)

4. The method according to claim 1 wherein the trisalkyl tin 1,2,4-triazole is tributyl tin 1,2,4-triazole of the formula

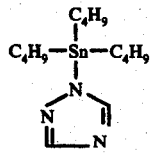 (2)

5. The method according to claim 1 wherein the trisalkyl tin 1,2,4-triazole is triisopropyl tin 1,2,4-triazole of the formula

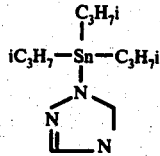 (3)

6. The method of claim 1 wherein the trisalkyl tin 1,2,4-triazole is tri-t-butyl tin 1,2,4-triazole of the formula

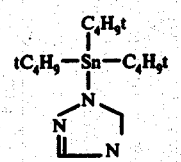 (4)

7. The method according to claim 1 wherein the trisalkyl tin 1,2,4-triazole is tricyclopentyl tin 1,2,4-triazole of the formula

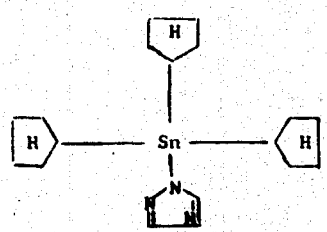 (5)

8. An insecticidal or acaricidal composition comprising an insecticidally or acaricidally effective amount of a trisalkyl tin 1,2,4-triazole of the formula

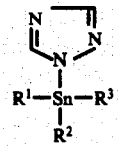 (I)

in which
R$^1$, R$^2$ and R$^3$ each independently is branched alkyl or cycloalkyl of 3 to 6 carbon atoms,
in combination with a solid or liquid diluent.

9. A composition according to claim 8 wherein said trisalkyl tin 1,2,4-triazole is a member selected from the group consisting of:
tricyclohexyl tin 1,2,4-triazole,
triisopropyl tin 1,2,4-triazole,
tri-t-butyl tin 1,2,4-triazole, and
tricyclopentyl tin 1,2,4-triazole.

* * * * *